US009155519B1

United States Patent
Tamura

(10) Patent No.: US 9,155,519 B1
(45) Date of Patent: *Oct. 13, 2015

(54) METHODS AND APPARATUS FOR ULTRASOUND IMAGING

(75) Inventor: Tadashi Tamura, North Haven, CT (US)

(73) Assignee: HITACHI ALOKA MEDICAL, LTD., Tokyo (JP)

( * ) Notice: Subject to any disclaimer, the term of this patent is extended or adjusted under 35 U.S.C. 154(b) by 468 days.

This patent is subject to a terminal disclaimer.

(21) Appl. No.: 13/079,417

(22) Filed: Apr. 4, 2011

Related U.S. Application Data

(60) Provisional application No. 61/320,996, filed on Apr. 5, 2010.

(51) Int. Cl.
*A61B 8/00* (2006.01)
*A61B 8/08* (2006.01)
*G01S 7/52* (2006.01)

(52) U.S. Cl.
CPC ............. *A61B 8/085* (2013.01); *G01S 7/52095* (2013.01)

(58) Field of Classification Search
CPC ........ A61B 8/085; A61B 8/485; A61B 8/488; G01S 7/52042; G01S 7/5209; G01S 7/52095
USPC .................. 600/407, 437, 440, 441, 453–457
See application file for complete search history.

(56) References Cited

U.S. PATENT DOCUMENTS

| 5,027,122 | A |   | 6/1991 | Wieler |
| 5,383,463 | A | * | 1/1995 | Friedman ...................... 600/455 |
| 6,280,387 | B1 | * | 8/2001 | Deforge et al. ............... 600/454 |
| 8,480,590 | B2 | * | 7/2013 | Tamura ......................... 600/457 |
| 2003/0125624 | A1 |   | 7/2003 | Shiki |
| 2006/0184032 | A1 |   | 8/2006 | Shiki |

FOREIGN PATENT DOCUMENTS

| JP | 2001224592 A | 8/2001 |
| JP | 2003061958 A | 3/2003 |
| WO | 2008/123596 A1 | 10/2008 |

OTHER PUBLICATIONS

M. Wuest et al., "A Variational De-Aliasing Technique", 2000, Phys. Chem. Earch (b), vol. 25, No. 10-12, Copyright 2000 Eisevier Science Ltd., PII: S1464-1909(00)00175-1, (pp. 1179-1183, total 5pgs.).

* cited by examiner

*Primary Examiner* — Mark Remaly
(74) *Attorney, Agent, or Firm* — Buckley, Maschoff & Talwalkar LLC

(57) ABSTRACT

Systems and methods are described to detect color flow areas, associated borders, and all flow image pixels inside the borders. Velocity aliasing correction may be performed based on an energy function determined using cross-border color Doppler data.

34 Claims, 14 Drawing Sheets

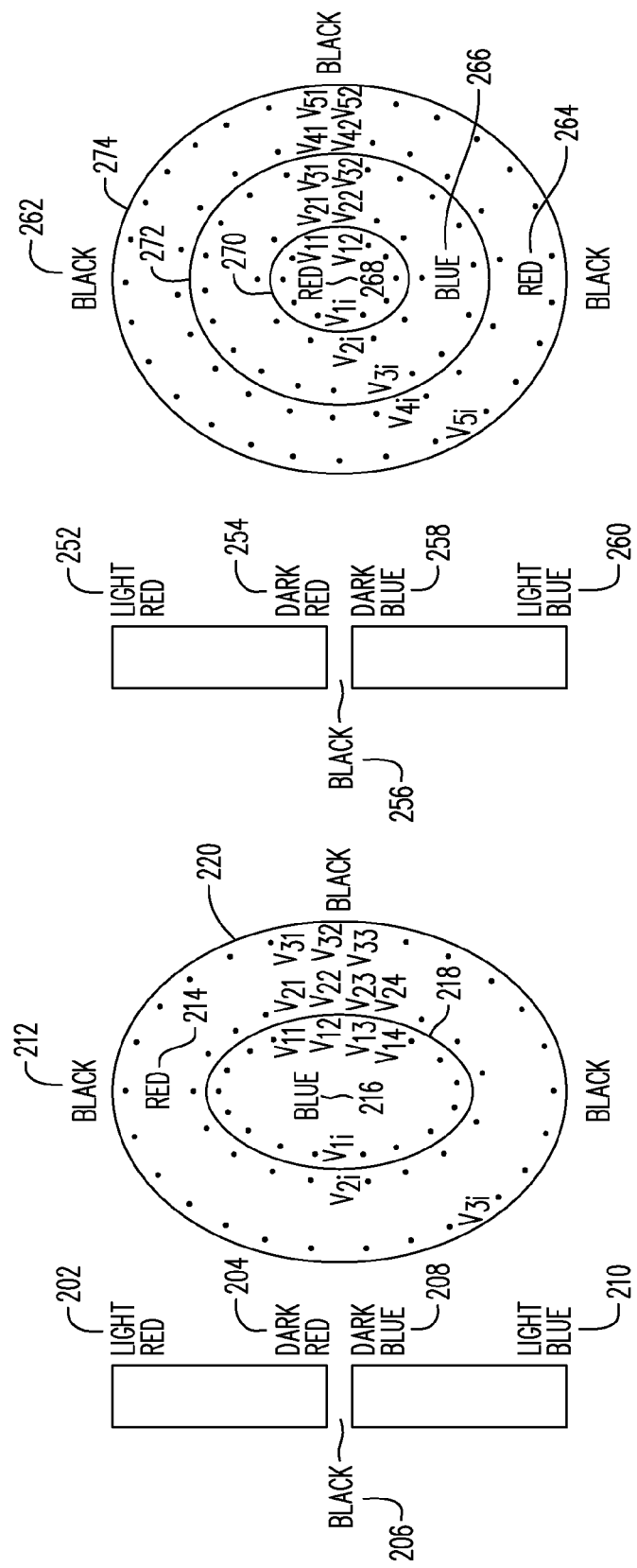

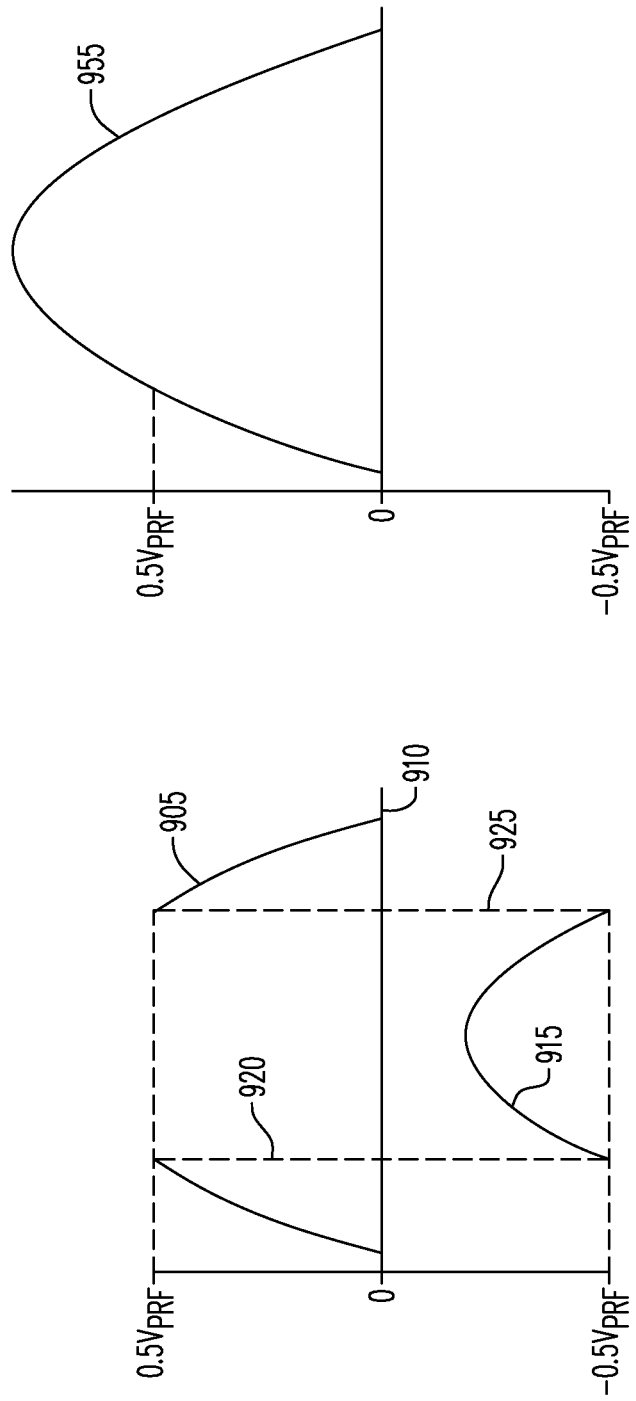

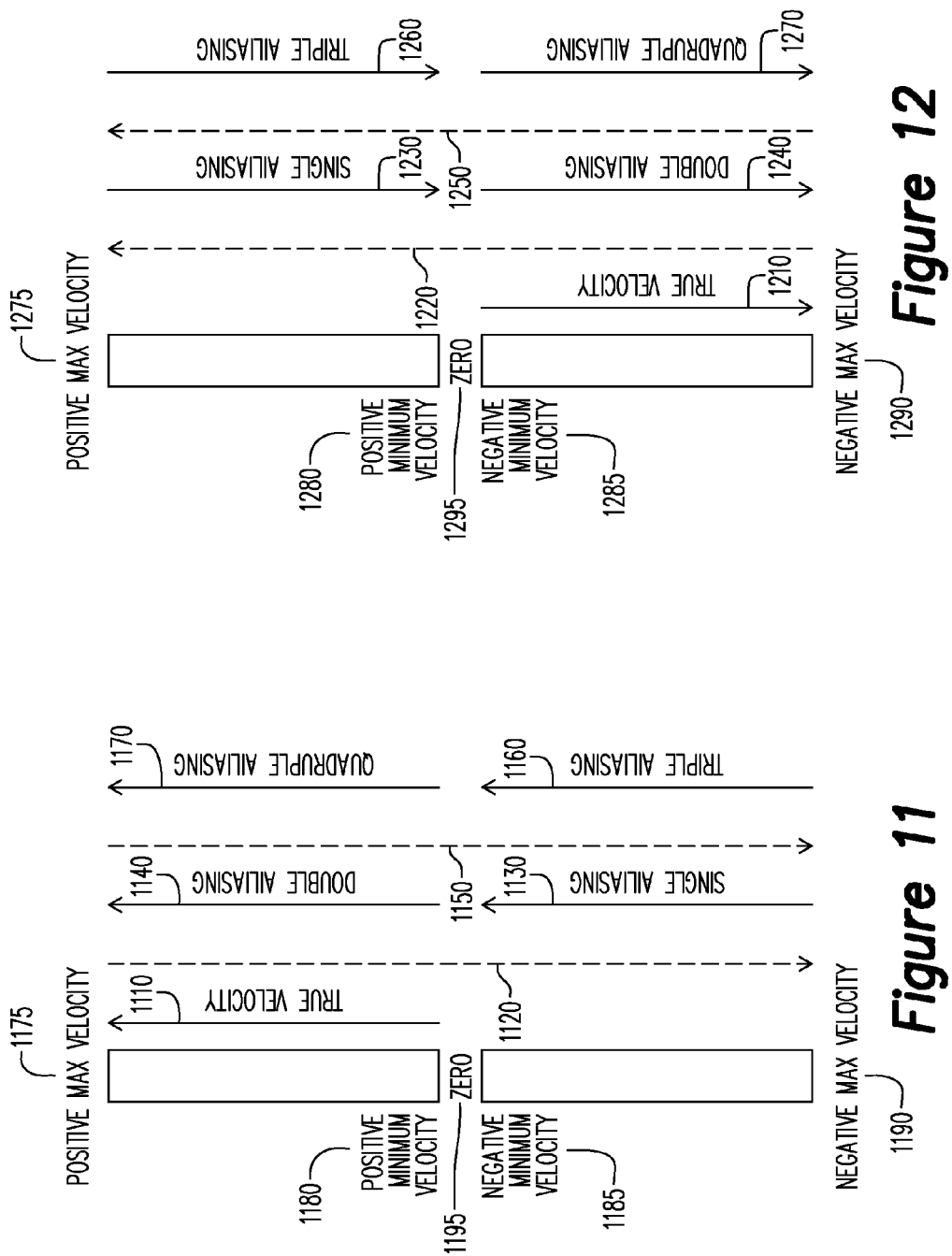

US 9,155,519 B1

METHODS AND APPARATUS FOR ULTRASOUND IMAGING

CROSS-REFERENCE TO RELATED APPLICATION

The present application claims priority to U.S. Provisional Patent Application Ser. No. 61/320,996, filed on Apr. 5, 2010 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for color flow imaging.

Ultrasound is used to image various internal structures, including but not limited to the heart, the liver, a fetus, and blood vessels. For diagnosis of cardiovascular diseases, color Doppler (or color flow) imaging is usually used to visualize blood flow in the heart or blood vessels. Abnormal conditions often increase blood flow velocity in comparison to blood flow velocity under normal conditions. The increased velocity may result in aliasing within a corresponding color Doppler image.

Color Doppler uses a pulse ultrasound technology for its spatial sampling capability, which limits the maximum frequency which can be detected without experiencing aliasing. This maximum frequency is determined by the pulse repetition frequency (PRF), which is the sampling frequency. The maximum frequency, in turn, limits the maximum blood flow velocity which can be measured without exhibiting aliasing.

This limitation may be particularly problematic in cardiac cases. For example, the PRF cannot be set high enough to measure abnormally high blood velocities that occur at substantial imaging depths such as, for example, regurgitation jets across heart valves. Therefore, under abnormal cardiac conditions, color Doppler often exhibits aliasing, thereby reducing the reliability of any diagnosis based on the blood flow image. Thus, there exists a need to address this aliasing problem.

BRIEF DESCRIPTION OF THE DRAWINGS

FIG. 2A: Color Doppler image with two flow areas.
FIG. 2B: Color Doppler image with three flow areas.

FIG. 9A: Color Doppler velocity distribution across a vessel with aliasing.
FIG. 9B: Color Doppler velocity distribution across a vessel with aliasing correction.
FIG. 11: Diagram of velocity aliasing of various degrees in the positive velocity direction.
FIG. 12: Diagram of velocity aliasing of various degrees in the negative velocity direction.

DETAILED DESCRIPTION

Figure 1B:
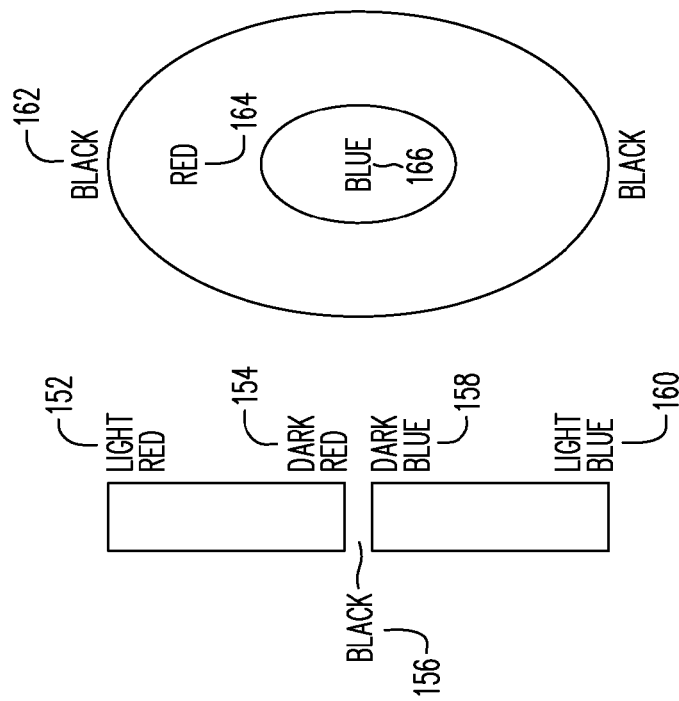
FIG. 1B: Color Doppler image with two flow areas.

Embodiments will be described with reference to the accompanying drawing figures wherein like numbers represent like elements throughout. Before embodiments of the invention are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that embodiments are not limited to any particular software language described or that is implied in the figures. One of ordinary skill in the art will understand that a variety of alternative software languages may be used for implementation of some embodiments. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

An ultrasound transducer transmits ultrasound (i.e., ultrasonic waves) into a human body to image various internal structures, including but not limited to blood vessels, a fetus, and the heart. Scatterers in tissue scatter the ultrasound and the scattered ultrasound is returned to the transducer. A receive beamformer receives ultrasound beams and a postprocessor creates an image of tissues based on the amplitude of the returned ultrasound signal as a B-mode image.

Blood vessels or the heart are often imaged, since they indicate cardiovascular conditions of patients. Blood flow information is usually acquired using color Doppler and spectral Doppler techniques.

Color Doppler is a two-dimensional imaging technique commonly used for imaging blood flow. Color Doppler operates by sending ultrasonic waves into the blood flow and detecting the scattered ultrasound from the moving red cells. It consists of many beams similar to a B-mode image. A description of a color Doppler technique now follows; embodiments are not limited to the specific details therein.

In order to detect flow velocity, an ultrasound transducer transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters and to create a two-dimensional flow image in linear and convex formats. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

In a color Doppler technique, the ultrasound is transmitted at a pulse repetition frequency (PRF) and the blood flow velocity at a position is detected as the shift in frequency (Doppler shift frequency) in the ultrasound signal received from the position. The received ultrasound is mixed with in-phase (0 degrees) and quadrature (90 degrees) reference signals of the same frequency as the transmit ultrasound frequency. After low-pass filtering high frequency components (e.g., second harmonics), only the baseband signals are obtained. Wall filtering (i.e., high-pass filtering) is applied to the baseband signals to remove strong clutter noise from tissue and slowly moving tissues such as blood vessel walls, resulting in complex I-Q Doppler signals. The wall filtering is performed because the Doppler I-Q signals may contain blood flow signal components as well as stationary tissue signal components. The stationary components are typically 30-40 dB greater than the blood flow components. Therefore, it is desirable to reduce or eliminate the stationary signal components in order to detect blood flow accurately.

Generally, the wall-filtered complex I-Q signal is used to derive the Doppler shift frequency because the Doppler shift frequency and the blood velocity have the following relationship $$\Delta f = \frac{2 f_t v \cos\theta}{c}, \tag{1}$$

where $\Delta f$ is the Doppler shift frequency, $f_t$ is the transmitted frequency, $v$ is the blood velocity, $\theta$ is the angle between the ultrasound beam direction and the velocity vector, and $c$ is the speed of sound.

In the case of color Doppler, the number of the sampled signals may be limited to 10. Therefore, an auto-correlation technique is usually used to determine the phase differences between the wall-filtered I-Q signal and then to determine the Doppler shift frequency and the blood flow velocity as follows. The color Doppler's I-Q signals $z(n)=x(n)+jy(n)$ are used to calculate "auto-correlation" R as shown in the following equation, where $z(n)$ is the wall-filtered complex I-Q Doppler signal, $x(n)$ is the in-phase (real) signal, $y(n)$ is the quadrature phase (imaginary) signal, n indicates the signal number, j is the imaginary unit and * indicates the complex conjugate.

$$R = \Sigma z(n) \cdot z^*(n+1) \tag{2}$$

The real (Real(R)) and imaginary (Imag (R)) parts of R are used to obtain the phase $\phi$ as shown in the following equation.

$$\varphi = \tan^{-1}\frac{\text{Imag}(R)}{\text{Real}(R)} \tag{3}$$

Since $\tan^{-1}$ usually provides only $-0.5\,\pi$ to $0.5\,\pi$, the position of complex value R in the complex coordinate may be also used to derive $\phi$ in the range of $-\pi$ to $\pi$. The phase $\phi$ is then related to the Doppler shift frequency as shown in the following equation.

$$\Delta f = \frac{\varphi f_{PRF}}{2\pi} \tag{4}$$

The Doppler shift frequency determined for a position indicates the blood flow velocity at the position. Additionally, the power of the high-pass filtered Doppler I-Q signals indicates the existence of blood flow and the variance of the data indicates turbulence. Other techniques can be used to obtain the phase, the Doppler shift frequency and the blood flow velocity.

Because the color Doppler signals are obtained by the pulsed ultrasound (and also sampling) technique, sampling theory dictates a maximum frequency limit. The maximum frequency is generally half of the pulse repetition frequency (PRF) or $f_{PRF}$. Since the autocorrelation is performed on the complex I-Q Doppler signals, blood flow velocity in a negative direction appears in the negative frequency domain. Therefore, the color Doppler frequency includes negative frequencies that correspond to negative velocities (i.e., velocities having a direction away from the ultrasound transducer). For example, the Doppler shift frequency usually has a range of $$-\frac{f_{PRF}}{2}$$

to $$\frac{f_{PRF}}{2},$$

which in turn corresponds to a range of negative and positive (i.e., velocities having a direction towards the ultrasound transducer) maximum velocities.

Some embodiments employ other Doppler shift frequency ranges. For example, the range may incorporate a "baseline shift" in which the center frequency of the range is not equal to zero. In some embodiments, the baseline shift may be selected from a range of frequencies between $$-\frac{f_{PRF}}{2}$$

and $$\frac{f_{PRF}}{2}.$$

Figures 8A, 8B, 8C:
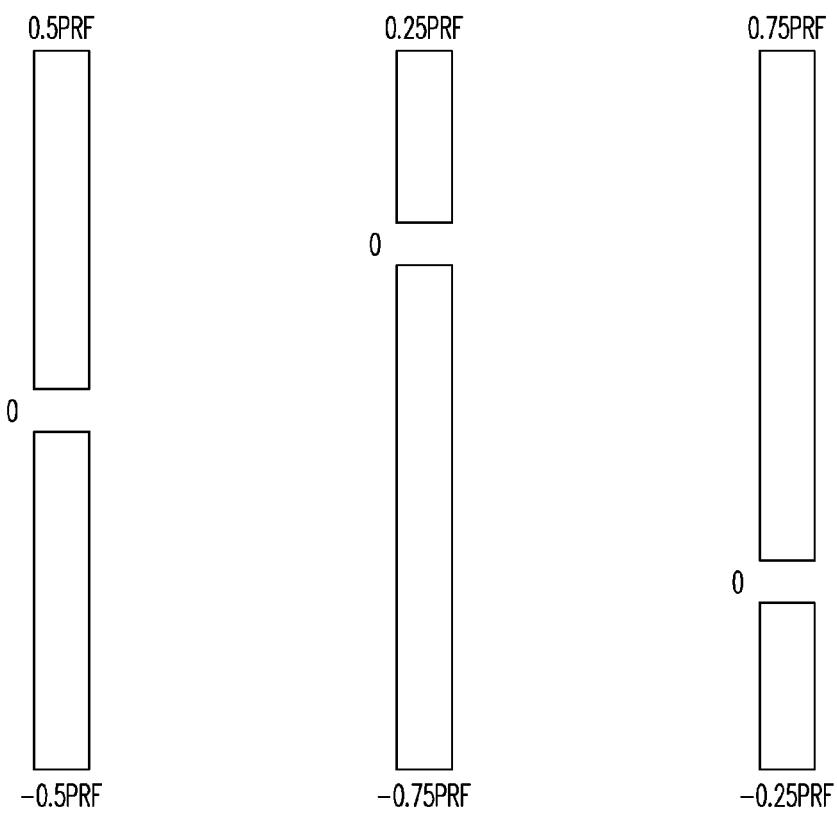
FIG. 8A: Color-coded Doppler shift frequency (velocity) scale with no baseline shift.
FIG. 8B: Color-coded Doppler shift frequency (velocity) scale with a baseline shift of $$\frac{f_{PRF}}{4}.$$
FIG. 8C: Color-coded Doppler shift frequency (velocity) scale with a baseline shift of $$-\frac{f_{PRF}}{4}.$$

In a particular example as shown in FIG. 8C, a Doppler shift frequency range of $$-\frac{f_{PRF}}{4}$$

to $$\frac{3f_{PRF}}{4}$$

reflects a baseline shift of $$-\frac{f_{PRF}}{4}.$$

This Doppler frequency range is associated with a negative maximum velocity corresponding to $$-\frac{f_{PRF}}{4}$$

and a positive maximum velocity corresponding to $$\frac{3f_{PRF}}{4}.$$

Similarly, a Doppler shift frequency range of $$-\frac{3f_{PRF}}{4}$$

to $$\frac{f_{PRF}}{4}$$

reflects a baseline shift of $$\frac{f_{PRF}}{4}$$

as shown in FIG. 8B. This Doppler frequency range is associated with a negative maximum velocity corresponding to $$-\frac{3f_{PRF}}{4}$$

and a positive maximum velocity corresponding to $$\frac{f_{PRF}}{4}.$$

FIG. 8A corresponds to the Doppler shift frequency ranges of FIGS. 1A, 1B, 2A and 2B, in which the baseline (i.e., 0 Hz) is in the center of the Doppler shift frequency (velocity) scale. When the baseline is shifted, e.g. by $$\frac{f_{PRF}}{4}$$

as shown in FIG. 8B, the positive maximum frequency becomes $$\frac{f_{PRF}}{4}$$

while the negative maximum frequency becomes $$-\frac{3f_{PRF}}{4}.$$

If the baseline shift is $$-\frac{f_{PRF}}{4},$$

the positive maximum frequency becomes $$\frac{3f_{PRF}}{4}$$

while the negative maximum frequency decreases to $$-\frac{f_{PRF}}{4}$$

as shown in FIG. 8C. In other words, the positive maximum frequency is decreased by the baseline shift while the absolute magnitude of the negative maximum frequency is increased by the baseline shift.

Often in cardiovascular applications, as well as in other applications, blood velocities may exceed these maximum velocities, resulting in aliasing. Color Doppler imaging uses color coding methods to represent blood velocities (or corresponding Doppler shift frequencies) at given positions within an image. For example, a particular blood flow velocity may be determined as described above for a particular position of an imaged region (e.g., a heart valve). A Color Doppler image of the region includes one or more pixels which represent the particular position. The one or more pixels are therefore colored based on the particular blood flow velocity determined for the position. More generally, each pixel of the Color Doppler image is assigned a color, and the color assigned to a pixel is associated with a flow velocity determined for the position represented by the pixel.

Figure 1A:
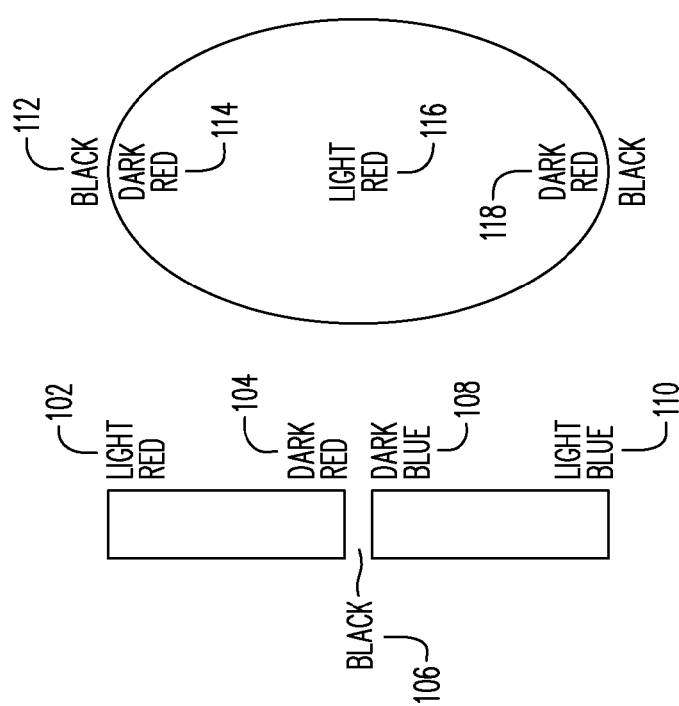
FIG. 1A: Color Doppler image.

With respect to FIG. 1A, positive velocities may be displayed in shades of red, with higher positive velocities represented by lighter red and lower positive velocities represented by darker red, while negative velocities may be displayed in shades of blue, with higher negative velocities represented by lighter blue and lower negative velocities represented by darker blue as shown in the color coding bars in the left hand side of FIG. 1A. Other color coding methods can be used to represent blood flow velocities.

FIG. 1A depicts a Doppler shift frequency range of $$-\frac{f_{PRF}}{2}$$

to $$\frac{f_{PRF}}{2}.$$

Therefore, the Doppler data of FIG. 1A is associated with a baseline shift of 0 Hz (i.e., no baseline shift). As mentioned above, embodiments are not limited thereto. A color flow image in the right hand side of FIG. 1A includes shades of red and apparently is not aliased.

When aliasing occurs, the color flow image may "wrap around" at velocities corresponding to the positive maximum frequency, with velocities corresponding to frequencies which exceed the positive maximum frequency represented by colors associated with negative velocities (e.g., shades of blue). Conversely, aliasing may cause velocities corresponding to frequencies which exceed (in absolute value) the negative maximum frequency to be represented by colors associated with positive velocities (e.g., shades of red). Aliasing therefore complicates the blood velocity image and makes any diagnosis based thereon difficult. FIG. 1B may show a color flow image which most likely includes aliasing. The center area is colored by shades of blue and surrounded by an area of shades of red which is then surrounded by areas of black. In this case, the center flow area of shades of blue is most likely aliased.

In some embodiments, aliased velocities are corrected as follows. With reference to FIG. 2A, flow velocities (e.g., $V_{11}$, $V_{12}$, ... ) are obtained near a transition from red colors (positive velocities) to blue colors (negative velocities). These flow velocities are associated with the colors of the image pixels located near the transition as described above. Although the color of each image pixel is based on a flow velocity associated with the image pixel's position, each image pixel may also be assigned a flow velocity. Such a situation may occur if a one-to-one correspondence does not exist between colors and flow velocities. For example, a single color may represent a range of flow velocities, in which case it may be beneficial to assign a flow velocity as well as a color to each pixel. Of course, each pixel may be assigned a flow velocity and a color even in embodiments in which colors and flow velocities share a one-to-one correspondence.

$V_{11}, V_{12}, \ldots V_{1i}$ are associated with pixels on the blue color side of the transition and are sampled at an equal spatial distance while $V_{21}, V_{22}, \ldots V_{2i}$ are associated with pixels on the red side of the transition and sampled at an equal spatial distance. $V_{1i}$ and $V_{2i}$ may be very close to each other across the transition. In some embodiments, velocities are sampled at unequal spatial distances.

The following energy function (5) across the transition is then calculated. As shown, the function determines the sum of the absolute velocity differences across the transition.

$$\sum_{i=1}^{n} |V_{1i} - V_{2i}|, \tag{5}$$

where n is the number of velocity samples.

The energy function (5) may be replaced by the following power function $$\sum_{i=1}^{n} (V_{1i} - V_{2i})^2 \tag{6}$$

or $$\sum_{i=1}^{n} (V_{1i} - V_{2i})^p \tag{7}$$

Flow velocities ($V_{31}, V_{32}, \ldots V_{3i}$) are also obtained near the transition from red colors (positive velocities) to black (zero velocities). Since the velocities associated with the black area are zero, function (5) reduces to $$\sum_{i=1}^{n2} |V_{3i}|, \tag{8}$$

where n2 is the number of velocity samples.

All of the energy functions determined for the FIG. 2A color flow image are linearly summed to create a total energy function. For example, $$\sum_{i=1}^{n} |V_{1i} - V_{2i}| + \sum_{i=1}^{n2} |V_{3i}| \tag{9}$$

In an alternate embodiment, (9) may be replaced by the following energy function (10), in which the energy functions associated with each transition are weighted with weights $w_1$ and $w_2$.

$$w_1 \sum_{i=1}^{n} |V_{1i} - V_{2i}| + w_2 \sum_{i=1}^{n2} |V_{3i}| \tag{10}$$

Next, it is assumed that some contiguous area of a single flow direction is aliased. For example, it may be assumed that the blue area in FIG. 2A is aliased. Each velocity of the assumed-to-be-aliased area is corrected by adding a velocity ($V_{PRF}$) corresponding to a Doppler shift frequency of the pulse repetition frequency, if the aliased velocity is negative, or by subtracting a velocity ($V_{PRF}$) corresponding to a Doppler shift frequency of the pulse repetition frequency if the aliased velocity is positive. In the case of FIG. 2A, $V_{1i}$ are replaced by $V_{1i}+V_{PRF}$ and the total energy function becomes $$\sum_{i=1}^{n} |V_{1i} + V_{PRF} - V_{2i}| + \sum_{i=1}^{n2} |V_{3i}| \tag{11}$$

or $$w_1 \sum_{i=1}^{n} |V_{1i} + V_{PRF} - V_{2i}| + w_2 \sum_{i=1}^{n2} |V_{3i}|. \tag{12}$$

A magnitude of total energy function (11) is compared with the magnitude of energy function (9). In some embodiments, the smaller magnitude is associated with the "correct" (i.e., non-aliased) color flow image. That is, FIG. 2A is assumed to be correct and non-aliased if the magnitude of energy function (9) is less than the magnitude of total energy function (11) (or (12)), otherwise the above-described corrected version of FIG. 2A is assumed to be non-aliased.

In some embodiments, another total energy function may be calculated for the case of FIG. 2A as follows, $$\sum_{i=1}^{n} |V_{1i} - (V_{2i} - V_{PRF})| + \sum_{i=1}^{n2} |V_{3i} - V_{PRF}|, \tag{13}$$

where the red colors ($V_{2i}$ and $V_{3i}$) are assumed to be aliased. As previously discussed, aliasing of positive velocities is corrected by subtracting $V_{PRF}$ from the aliased velocities. The total energy function (13) may be greater than the total energy functions (11) or (9). The comparison of three total energy function may yield the following result.

Energy function(11)<Energy function(9)<Energy function(13)

The total energy function (11) is smallest and therefore it is determined that its underlying assumption (i.e., the blue area is aliased) is correct. The total energy function (13) may be replaced with weighted energy function (14) as follows and a comparison among total energy functions (10), (12) and (14) may be made.

$$w_1 \sum_{i=1}^{n} |V_{1i} - (V_{2i} - V_{PRF})| + w_2 \sum_{i=1}^{n2} |V_{3i} - V_{PRF}| \tag{14}$$

The total energy may indicate the velocity differences or gradients across the transitions. Flow or blood flow must follow physics or fluid mechanics laws. For example, flow velocity cannot change too rapidly spatial-wise, meaning velocity gradients or differences cannot be too large. FIG. 9A shows an example of velocities measured by color Doppler techniques. The horizontal axis is a spatial coordinate (for example, a vessel diameter) and the vertical axis is color Doppler velocity. At the left spatial point, the velocity is virtually zero (0) and then increases gradually as the spatial point moves to the right until the velocity reaches $0.5V_{PRF}$ and then suddenly changes to $-0.5V_{PRF}$. Then, the velocity increases from $-0.5V_{PRF}$ to approximately $-0.2 V_{PRF}$ and then decreases back to $-0.5 V_{PRF}$. When the velocity reaches $-0.5 V_{PRF}$, it suddenly jumps back to $0.5 V_{PRF}$.

FIG. 9A therefore represents a typical example of aliasing. There are two transitions, from $0.5 V_{PRF}$ to $-0.5 V_{PRF}$ and from $-0.5 V_{PRF}$ to $0.5 V_{PRF}$. At the transitions, the velocity differences are very large. If velocity is spatially continuously sampled, the velocity difference across the transition is $V_{PRF}$. The negative velocities in FIG. 9A are all aliased. If this aliasing is corrected, the correct velocity distribution (profile) may be obtained as shown in FIG. 9B. The velocity difference across the old transition is very small, and may approach zero. FIGS. 9A and 9B show velocity distributions in one-dimension for simplicity. The determination of the smallest total energy function as discussed above may represent searching for a solution for an optimal (most likely) 2-dimensional velocity distribution which is without aliasing.

A more complicated case is shown in FIG. 2B. In this example, the center area includes shades of red, indicating positive velocities, and is surrounded by a ring-like area of shades of blue, which in turn is surrounded by another ring-like area of shades of red, which is surrounded by black areas. Therefore, FIG. 2B illustrates three transitions. Velocities on one side of the first transition are marked by $V_{11}, V_{12}, \ldots, V_{1i}\ldots$, while corresponding velocities on the other side of the first transition are marked by $V_{21}, V_{22}, \ldots, V_{2i}, \ldots$. An energy function across the first transition is obtained as follows, $$\sum_{i=1}^{n} |V_{1i} - V_{2i}|, \tag{15}$$

where n is the number of velocity samples.

Velocities on the blue-shaded side of the second transition are marked by $V_{31}, V_{32}, \ldots, V_{3i}, \ldots$, while the corresponding velocities of the red-shaded side of the second transition are marked by $V_{41}, V_{42}, \ldots V_{4i}\ldots$. An energy function across the second transition is obtained as follows, $$\sum_{i=1}^{n2} |V_{3i} - V_{4i}|, \tag{16}$$

where n2 is the number of velocity samples.

Velocities on the red-shaded side of the third transition are marked by $V_{51}, V_{52}, \ldots V_{5i} \ldots$, while the black areas represent zero velocities. A corresponding energy function for the third transition is therefore obtained as follows, $$\sum_{i=1}^{n3} |V_{5i}|, \tag{17}$$

where n3 is the number of velocity samples.

The total energy function may be obtained as follows, $$\sum_{i=1}^{n} |V_{1i} - V_{2i}| + \sum_{i=1}^{n2} |V_{3i} - V_{4i}| + \sum_{i=1}^{n3} |V_{5i}|. \tag{18}$$

As described above, aliasing corrections may be applied to various combinations of the velocity areas until the smallest total energy function is determined. All velocities of the same area are corrected the same way, so if $V_{PRF}$ is added to a velocity of an area, $V_{PRF}$ is added to all other velocities in the same area.

Flow velocities may "wrap around" the velocity limits (maximum and minimum velocity magnitude) more than once, in that they exceed the maximum velocity and the minimum velocity of the opposite velocity direction. FIGS. 11 and 12 illustrate such "double-aliasing", "triple-aliasing" and "quadruple-aliasing", in addition to the previously-described "single-aliasing". For example, positive velocities may exceed the positive maximum velocity and wrap around to the negative maximum velocity as shown by the dotted arrow 1120. The velocity range 1110 shows a true velocity range. Once the aliasing occurs, the velocity range becomes "single-aliased" velocity range 1130 as shown in FIG. 11. The velocity then may further exceed zero velocity (or the negative minimum velocity limit) and change the velocity direction again, resulting in positive velocities which may be called "double-aliased" velocities 1140. Then the velocity may further exceed the positive maximum velocity again and wrap around to the negative maximum velocity as shown by the dotted arrow 1150. The velocity may further increase in the "triple-aliased" velocity range 1160. The velocity then may further increase and go across the zero velocity and change the velocity direction, resulting in the positive velocities which may be called "quadruple aliased" velocities. The above discussion of aliasing, "double-aliasing", "triple-aliasing", and "quadruple-aliasing" may also apply to the opposite direction as shown in FIG. 12.

For such aliasing, aliasing correction may include adding $V_{PRF}$ to the velocity if the "double-aliased" velocity is positive. If the double-aliased velocity is negative, $V_{PRF}$ is subtracted from the double-aliased velocity. Similarly, for "triple aliasing", $2V_{PRF}$ is subtracted from the triple-aliased velocity if the velocity is positive, and $2V_{PRF}$ is added to the triple-aliased velocity if the velocity is negative. For quadruple aliasing, $2V_{PRF}$ is added to the velocity if the velocity is positive, and $2V_{PRF}$ is subtracted from the velocity if the velocity is negative.

Aliasing corrections of various degrees (single aliasing, double aliasing, triple aliasing . . . ) may be applied to all or some of flow areas in FIG. 2B when determining the smallest the total energy function (18). For example, the following function $$\sum_{i=1}^{n} |(V_{1i} + V_{PRF}) - (V_{2i} + V_{PRF})| + \sum_{i=1}^{n2} |(V_{3i} + V_{PRF}) - V_{4i}| + \sum_{i=1}^{n3} |V_{5i}| \quad (19)$$

may yield a lower value than (18). In this total energy function (19), the red center area is assumed double-aliased, the blue ring-like area is assumed single aliased and no aliasing is assumed in the red ring-like area. Weights ($w_1$, $w_2$, $w_3$) may be also associated with each energy function. The same aliasing corrections are applied to all velocities of a continuous flow area of the same velocity direction (i.e., positive or negative) when the total energy function is calculated. For example, $V_{PRF}$ is added to all velocities inside the blue-ring area including $V_{21}$, $V_{22}$, . . . $V_{2i}$, . . . and $V_{31}$, $V_{32}$, . . . $V_{3i}$, . . . .

Figure 10:
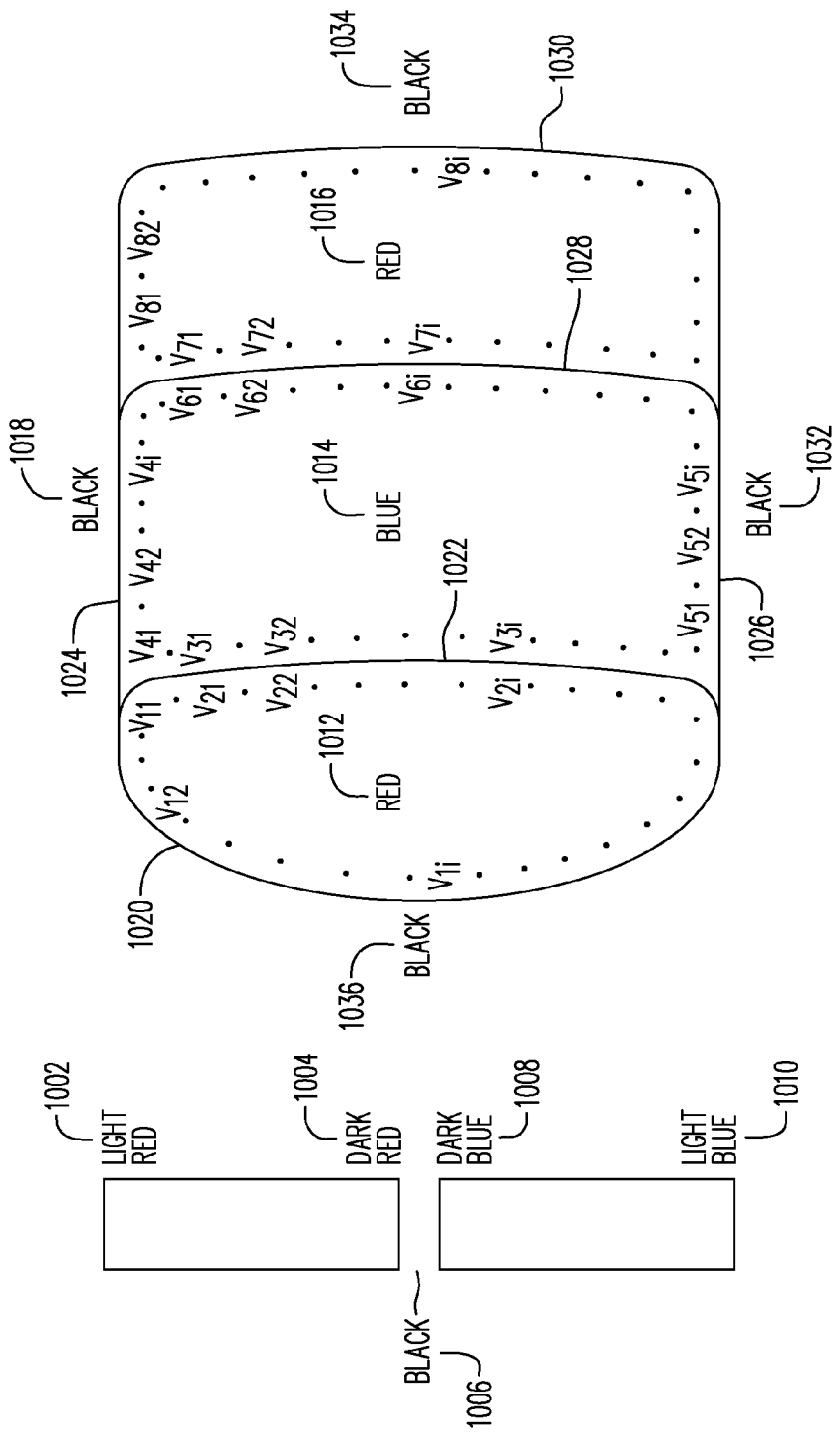
FIG. 10: Color Doppler image with three flow areas.

FIG. 10 illustrates a color flow image in which flow areas are divided into three areas of red shades, blue shades and red shades. The image includes a first transition between the black area and the left-most red-shaded area. Velocities adjacent to this transition are marked by $V_{11}$, $V_{12}$, . . . , $V_{1i}$, . . . . For this transition, an energy function may be obtained as follows, $$\sum_{i=1}^{n} |V_{1i}|, \quad (20)$$

where n is the number of velocity samples.

The second transition is between the left-most red-shaded area and the blue-shaded area. Velocities of the red-shaded side of the transition are marked by $V_{21}$, $V_{22}$, . . . , $V_{2i}$, while the corresponding velocities on the blue-shaded side of the transition are marked by $V_{31}$, $V_{32}$, $V_{3i}$, . . . . For this transition, an energy function may be obtained as follows, $$\sum_{i=1}^{n2} |V_{2i} - V_{3i}|, \quad (21)$$

where n2 is the number of velocity samples.

A third transition exists between the blue area and a black area at the top of the color flow image. Velocities on the blue-shaded side of the transition are marked $V_{41}$, $V_{42}$, . . . , $V_{4i}$, . . . while the black area has zero velocities. For this transition, an energy function may be obtained as follows, $$\sum_{i=1}^{n3} |V_{4i}|, \quad (22)$$

where n3 is the number of velocity samples.

The fourth transition is between the blue-shaded area and a black area at the bottom of the color flow image. Velocities on the blue-shaded side of the transition are marked $V_{51}$, $V_{52}$, . . . , $V_{5i}$, . . . while the black area has zero velocities. For this transition, an energy function may be obtained as follows, $$\sum_{i=1}^{n4} |V_{5i}|, \quad (23)$$

where n4 is the number of velocity samples.

A fifth transition exists between the blue-shaded area and the right-most red-shaded area. Velocities of the blue-shaded side of the transition are marked $V_{61}$, $V_{62}$, . . . , $V_{6i}$ . . . while velocities on the red-shaded side of the transition are marked by $V_{71}$, $V_{72}$, . . . , $V_{7i}$, . . . . For this transition, an energy function may be obtained as follows, $$\sum_{i=1}^{n5} |V_{6i} - V_{7i}|, \quad (24)$$

where n5 is the number of velocity samples.

The sixth transition is between the right-most red-shaded area and the black area. Velocities of the red-shaded side of the transition are marked by $V_{81}$, $V_{82}$, $V_{8i}$ . . . while the black area has zero velocities. For this transition, an energy function may be obtained as follows, $$\sum_{i=1}^{n6} |V_{8i}|, \quad (25)$$

where n6 is the number of velocity samples.
The total energy function may be obtained as follows, $$\sum_{i=1}^{n} |V_{1i}| + \sum_{i=1}^{n2} |V_{2i} - V_{3i}| + \quad (26)$$

$$\sum_{i=1}^{n3} |V_{4i}| + \sum_{i=1}^{n4} |V_{5i}| + \sum_{i=1}^{n5} |V_{6i} - V_{7i}| + \sum_{i=1}^{n6} |V_{8i}|$$

and aliasing corrections may be introduced to all or some of the flow areas as discussed previously. The same aliasing corrections are applied to all velocities inside the transitions or to velocities (i.e., positive or negative) of a same continuous flow area when calculating the total energy function. For example, $V_{PRF}$ may be added to $V_{31}, V_{32}, \ldots V_{3i} \ldots$ and $V_{41}$, $V_{42}, \ldots V_{4i}, \ldots$ and $V_{51}, V_{52}, \ldots, V_{5i}$ and $V_{61}, V_{62}, \ldots$, $V_{6i} \ldots$ for the case of FIG. 10. As described above, those aliasing corrections which result in a smallest total energy function are considered to reflect the true flow velocity conditions.

Figure 13:
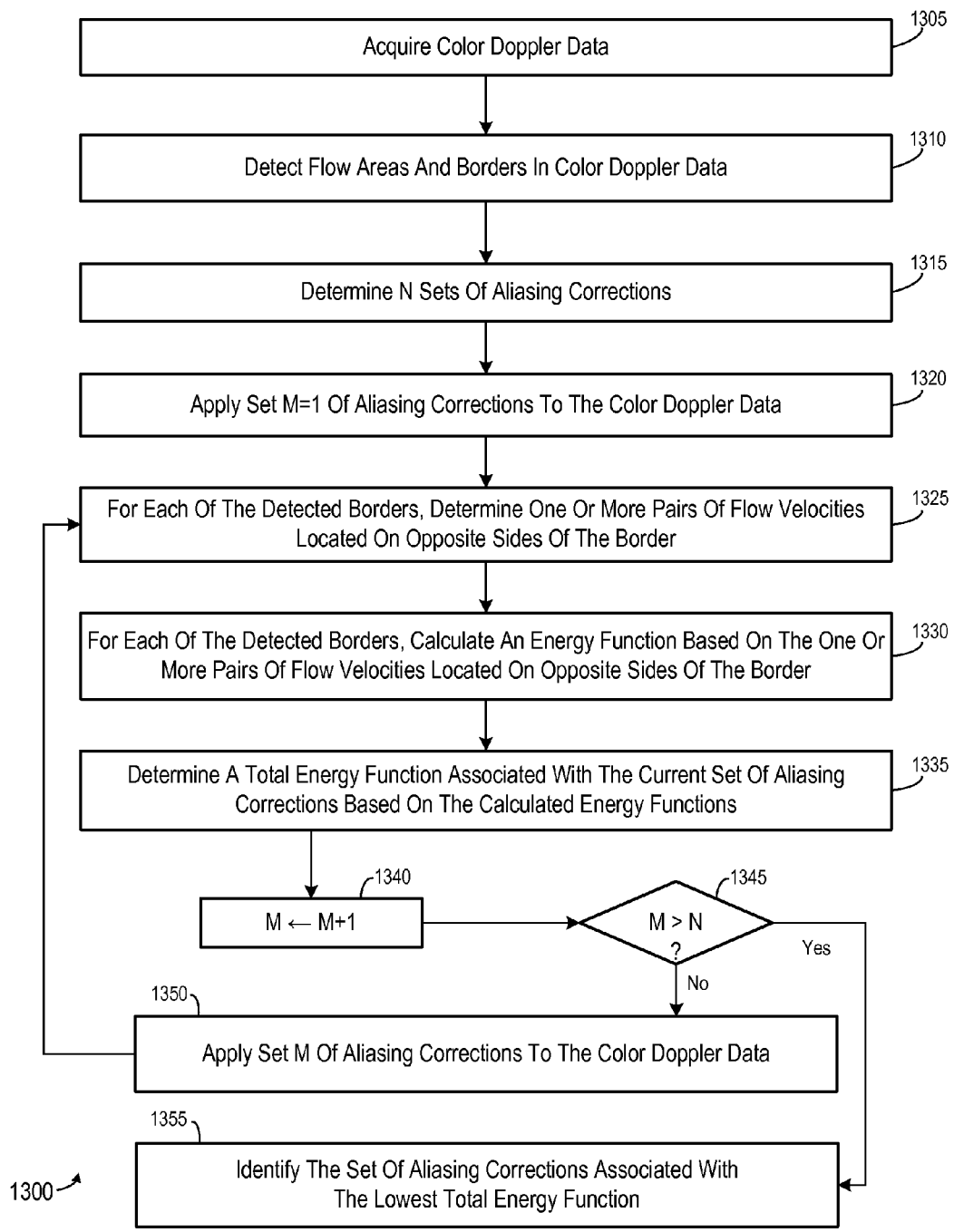
FIG. 13: Flow diagram of a process to address aliasing correction according to some embodiments.

FIG. 13 is a flow diagram of a process 1300 to describe the aliasing correction method previously discussed. First, color Doppler data including color flow lines or color Doppler images may be acquired at 1305. The data includes pixels, with each pixel associated with an image position and with a flow velocity. The flow velocity may be represented by an assigned color, a number, or by any other means. Flow areas and flow area borders in the color Doppler data are detected at 1310. Detection of flow areas and borders according to some embodiments will be described below with respect to FIG. 14. In the foregoing description of FIG. 13, it will be assumed that each pixel is associated with an image position, a flow velocity, and a border or flow area to which it belongs.

Several (e.g., N=a positive integer) sets of aliasing corrections are determined at 1315. A set of aliasing corrections includes one aliasing correction (e.g., $0 V_{PRF}$, $+/-V_{PRF}$, $+/-2 V_{PRF}$, $+/-3 V_{PRF}$, $+/-4 V_{PRF}$, $+/-5 V_{PRF}$) to be applied to color Doppler data within each of the detected flow areas.

When determining the N sets of aliasing corrections, the maximum degree of aliasing and its correction is limited to save computation time. All possible combinations of flow areas and degree of aliasing (e.g. no aliasing, single aliasing and up to the maximum degree of aliasing) are considered in the determination of the aliasing correction sets. As will be described below, a total energy function is determined for each one of the determined sets of aliasing corrections.

In some embodiments, the possible sets of aliasing corrections may include only particular degrees of aliasing correction (e.g., no aliasing to quadruple aliasing or $0 V_{PRF}$, $+/-V_{PRF}$, $+/-2 V_{PRF}$) in order to reduce processing workload.

A first set of aliasing corrections (i.e., M=1) is applied to the acquired color Doppler data at 1320. The first set of aliasing corrections may include no aliasing corrections, so that the "corrected" color Doppler data is identical to the originally-acquired color Doppler data.

For each detected border segment, one or more pairs of flow velocities located on opposite sides of the border segment are located at 1325. Next, and also for each border segment, an energy function is calculated at 1330 based on the one or more pairs of flow velocities (or color Doppler values, i.e., the Doppler shift frequency or the color Doppler phase) located on opposite sides of the border segment. As described above, this calculation may be based on the sum of the absolute differences of the one or more pairs of flow velocities located on opposite sides of the border segment.

According to some embodiments, the number of flow velocities on each side of the border segment need not be identical. Consequently, a same flow velocity on a side of the border segment may belong to more than one of the one or more pairs of flow velocities. For example, with respect to FIG. 2B, calculation of an energy function at 1330 may include determination of an absolute difference between flow velocity pair $(V_{31}, V_{41})$ and of an absolute difference between flow velocity pair $(V_{31}, V_{42})$.

A total energy function associated with the first set of aliasing corrections is determined at 1335. In some embodiments, the total energy function is the sum of all the energy functions determined for all the border segments and for the first set of aliasing corrections. Determination of the total energy function at 1335 may include weighting one or more of the individual energy functions as described previously.

1340 and 1345 are intended to simply describe selection of a next set of aliasing corrections, if any, from the determined N sets of aliasing corrections. Embodiments are not limited to the specific mechanisms described with respect to 1340 and 1345. In particular, at 1340, a counter (i.e., M) representing the previously-applied set of aliasing corrections is incremented by one (i.e., M←M+1) to indicate a next set of aliasing corrections. If it is determined at 1345 that the value of the counter is greater than N, then a respective total energy function has been determined for each of the determined N sets of aliasing corrections. If not, the next set of aliasing corrections is applied to the originally-acquired color Doppler data at 1350 and flow returns to 1325 to determine one or more pairs of "corrected" flow velocities for each border segment and to calculate an energy function for each border segment at 1330.

Flow continues as described above to determine a total energy function associated with the latest set of aliasing corrections at 1335. This loop repeats to determine a total energy function associated with each candidate set of aliasing corrections, until it is determined at 1345 that no more sets of aliasing corrections are to be evaluated because M is greater than N (M>N).

Flow then proceeds to 1355 to identify a set of aliasing corrections associated with the lowest total energy function. According to some embodiments, this identified set of aliasing corrections is assumed to be correct, and is therefore applied to the originally-acquired color Doppler data in order to correct any aliasing exhibited thereby.

Figure 6B:
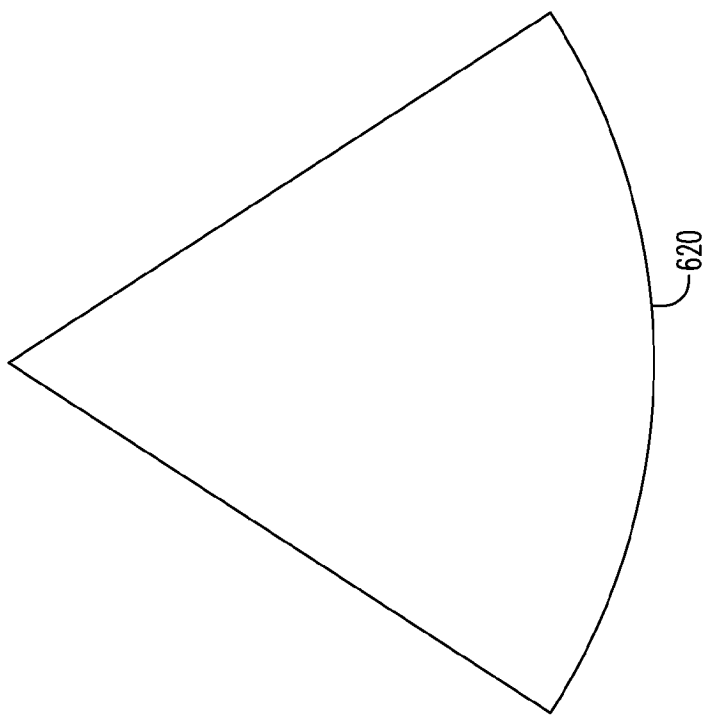
FIG. 6B: A representation of a scan-converted color flow image.
Figure 6A:
FIG. 6A: A representation of color flow lines.
Figure 7B:
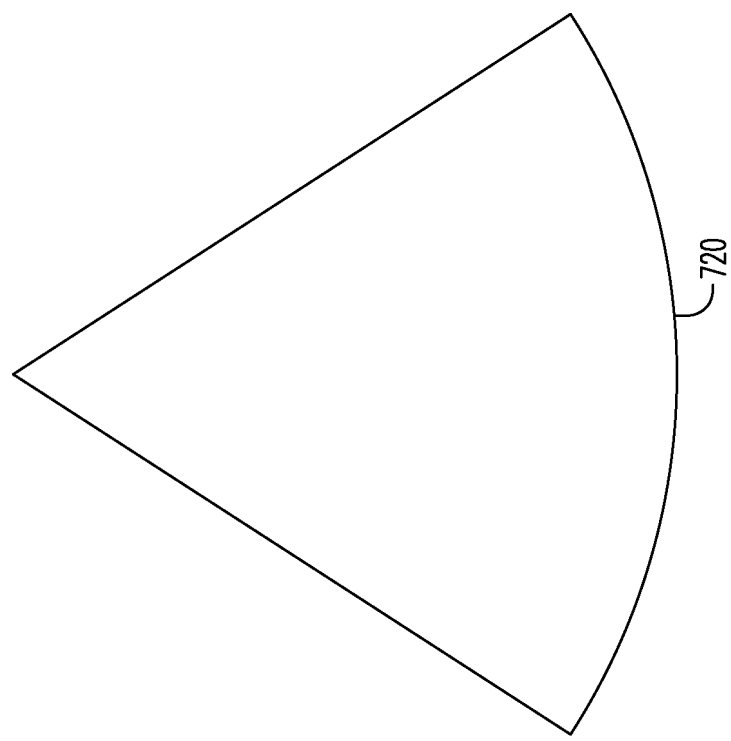
FIG. 7B: A representation of a scan-converted B-mode image.
Figure 7A:
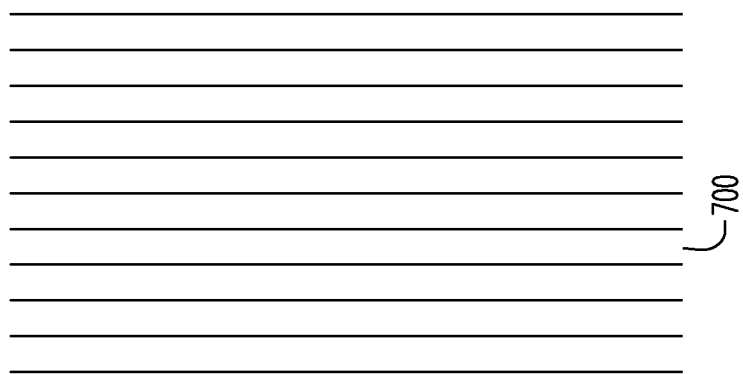
FIG. 7A: A representation of B-mode lines.

As mentioned above, the method may be applied to color flow line data or color Doppler image data according to some embodiments. FIG. 6A shows color flow lines 600 before scan-conversion, although only 11 lines are shown as an example. A color flow line consists of many color flow data samples along the line. Color flow lines are created from color beam data and may not show correct spatial dimensions. Scan-conversion is a technique to convert the color flow lines to a raster video image by interpolating the color flow lines. In a scan-converted image (e.g., sector scan) shown FIG. 6B, the color flow image consists of color flow image pixels of the orthogonal (x-y) coordinate with the correct length relationship (vertical vs. horizontal dimensions) in contrast to the color flow lines shown in FIG. 6A. B-mode imaging also uses the scan-conversion technique to convert B-mode lines as shown in FIG. 7A to a B-mode image as shown in FIG. 7B by interpolating B-mode line data.

Figure 14:
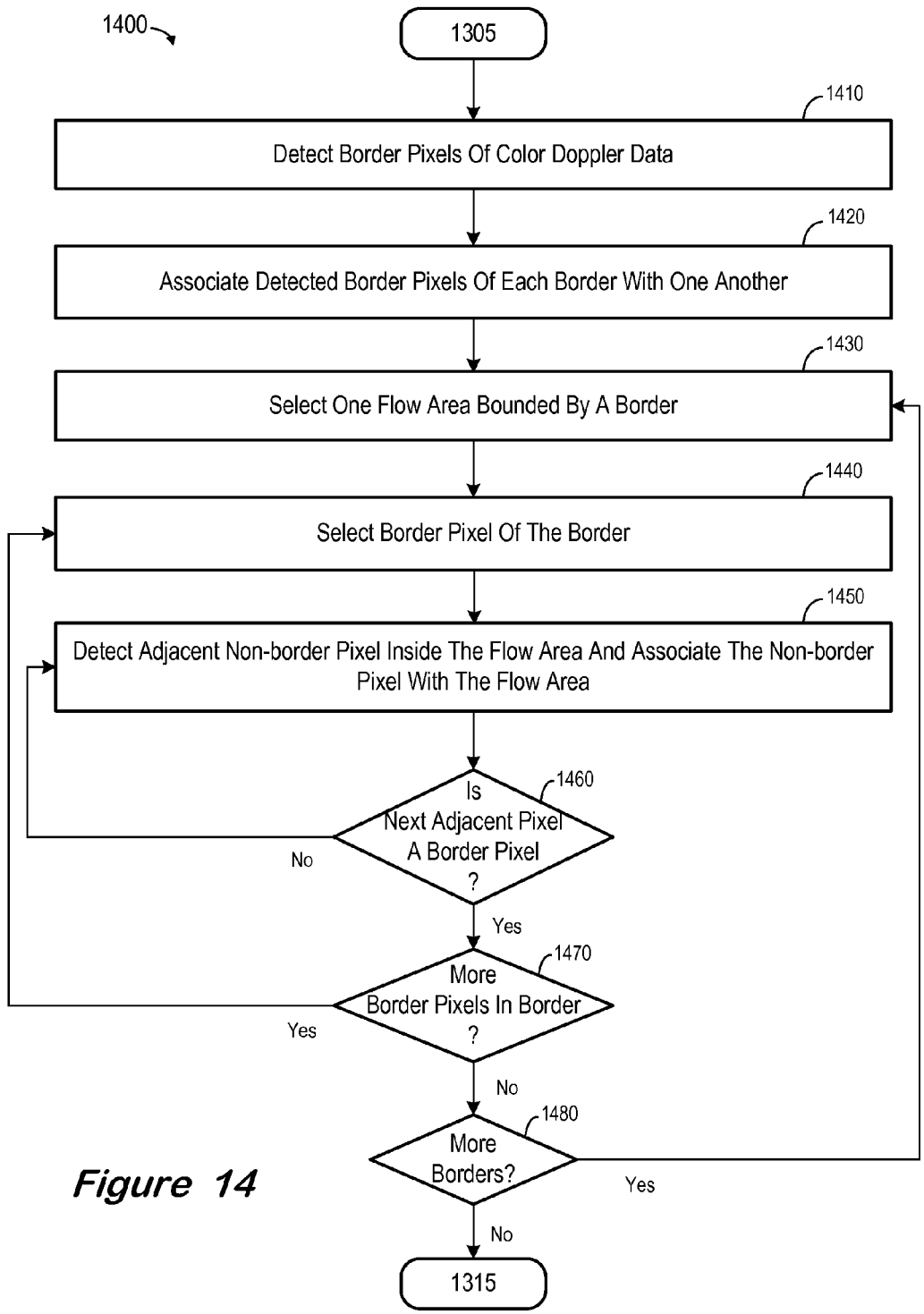
FIG. 14: Flow diagram of a process to detect flow areas and borders according to some embodiments.

Detection of the borders and the flow areas at 1310 according to some embodiments will now be described with reference to FIG. 14. Initially, at 1410, border pixels are detected within the color Doppler data. Detection of the border pixels may begin by identifying image pixels associated with positive velocities and which are disposed next to image pixels associated with either negative velocities or zero velocities.

Figure 15:
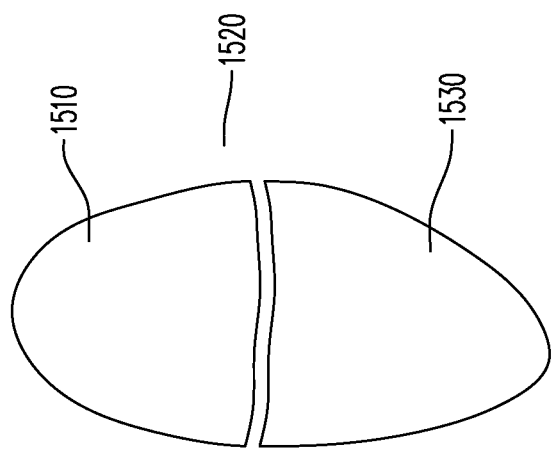
FIG. 15: Color Doppler image including two flow areas.

FIG. 15 shows a color Doppler flow image consisting of two flow areas including positive and negative color velocities. The top portion is an area 1510 of positive velocities surrounded by areas 1520 of zero velocities, and the bottom portion is an area 1530 of negative velocities.

The detected adjacent pixels of each border are then associated with one another at 1420. For example, each image pixel of a border may be associated with an identifier of the border. In some embodiments, adjacent image pixels of a border are also associated with one another. This association may allow further processing to easily determine which border pixels are "next to" and given border pixel.

In one example, the position and velocity of each detected pixel are stored in contiguous (or otherwise-linked) memory locations as follows:

$x_{R1}, y_{R1}, v_{R1}, R, RO, x_{RO1}, y_{RO1}, v_{RO1},$
$x_{R2}, y_{R2}, v_{R2}, R, RO, x_{RO2}, y_{RO2}, v_{RO2},$
$x_{R3}, y_{R3}, v_{R3}, R, RO, x_{RO3}, y_{RO3}, v_{RO3},$
. . . .
i) $x_{Ri}, y_{Ri}, v_{Ri}, R, RO, x_{ROi}, y_{ROi}, v_{ROi},$
. . . .
n) $x_{Rn}, y_{Rn}, v_{Rn}, R, RO, x_{ROn}, y_{ROn}, v_{ROn},$ where each pixel in the sequence is located physically-adjacent to the preceding and following pixels in the sequence, and where $x_{Ri}, y_{Ri}$ is the x-y coordinate of the image pixel of i-th pixel of the border, $v_{Ri}$ is the velocity of i-th border pixel, and R is an index identifying a flow region bordered by these pixels, (e.g., 1 in the present example).

RO is a Region number of Opposite flow or no flow next to the border pixel, which may be helpful in identifying the border pixel at 1410. The RO will help identify a transition between a positive velocity area and a negative velocity area or between zero velocity and a positive or a negative velocity by pairing a flow area and another flow area in a complex flow configuration as shown in FIG. 10. Accordingly, a single value of R may be associated with one or more values of RO. $x_{ROi}, y_{ROi}, v_{Roi}$ are the x-y coordinate and velocity of an border image pixel corresponding to the border image pixel with $x_{Ri}, y_{Ri}, v_{Ri}$ on the opposite side of the border.

For example, one border completely surrounding a flow area may be divided into several border segments (or transitions) as shown in FIG. 10. For the border in the center negative (blue) flow area 1014 in FIG. 10, a first border segment 1024 may be defined between an upper zero velocity area 1018 and a blue (negative) velocity area 1014 in the center. A second border segment 1028 may be defined between the negative velocity area 1014 and the positive velocity area 1016 to the right. A third border segment 1026 may be defined between the negative velocity area 1014 and a lower zero velocity area 1032. A fourth border segment 1022 may be defined between the negative velocity area 1014 and a positive velocity area 1012 to the left. Again, a border segment may be treated equivalently to the borders discussed herein.

1410 may further or alternatively include detection of all image pixels associated with negative velocities and which are disposed next to image pixels associated with either positive velocities or zero velocities. These detected adjacent pixels may be associated with one another at 1420 as described above. For example, the position and velocity of each detected pixel may be stored as follows, with R=2:

$x_{R1}, y_{R1}, v_{R1}, R, RO, x_{RO1}, y_{RO1}, v_{RO1},$
$x_{R2}, y_{R2}, v_{R2}, R, RO, x_{RO2}, y_{RO2}, v_{RO2},$
$x_{R3}, y_{R3}, v_{R3}, R, RO, x_{RO3}, y_{RO3}, v_{RO3},$
. . . .
i) $x_{Ri}, y_{Ri}, v_{Ri}, R, RO, x_{ROi}, y_{ROi}, v_{ROi},$
. . . .
m) $x_{Rm}, y_{Rm}, v_{Rm}, R, RO, x_{ROm}, y_{ROm}, v_{ROm},$

Image pixels comprising the border of each flow area may be thereby identified and stored in logical and spatial relation to one another.

Image pixels inside the flow areas may then be identified and stored as follows. Initially, at 1430, a flow area bounded by a detected border is selected. In this case, the flow area is a positive flow area. Next, at 1440, any border pixel of the border is selected. A pixel associated with a positive velocity and adjacent to the border pixel is detected at 1450 and its position, velocity and an identifier of the flow area are stored in association with the border pixel as described above. At 1460, it is determined whether the next adjacent flow image pixel is a border pixel (e.g., based on the previously-detected border information) and, if not, flow returns to 1450 and this pixel is stored as described above. In some embodiments, a detected "adjacent" pixel may extend in any direction from the "current" pixel, including but not limited to vertically, horizontally, diagonally, or otherwise.

Figure 16:
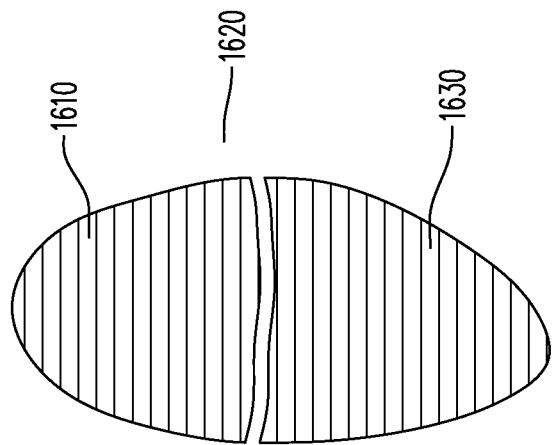
FIG. 16: Diagram to illustrate flow area detection in a color Doppler image.

FIG. 16 illustrates detection of horizontally-adjacent pixels along a horizontal line from a first border pixel. Upon reaching another border pixel on the other side of the flow area (e.g., at the right-hand side of area 1610), the determination at 1460 is positive (i.e., the next adjacent pixel is determined to be a border pixel) and flow proceeds to 1470. If the border includes more untested border pixels (i.e., border pixels which have not been selected at 1440 or detected at 1460), a next border pixel (e.g., adjacent to the prior selected border pixel or any one of the untested border pixels) is then selected at 1440 and flow cycles between 1450 and 1460 as described above to identify additional pixels of the flow area. Flow therefore cycles through 1440 to 1470 until all image pixels in the flow area are identified and stored.

Flow proceeds from 1470 to 1480 to select another flow area bounded by a border once all pixels of the current border have been selected at 1440 or detected at 1450 and all image pixels in the corresponding flow area are detected, identified (i.e., as belonging to the flow area) and stored. At 1480, if the Doppler data includes borders which have not been subjected to the processing of 1430 through 1470, flow returns to 1430 to select a flow area bounded by one of these borders. As a result, all pixels inside the borders of flow areas are identified. In the case of FIGS. 15 and 16, all pixels inside the borders of flow areas 1520 and 1530 (1610, 1630) are identified. Selection of a border pixel at 1440 may be performed at random or according to the order in which the border pixels are associated in memory. Also, selection of a flow area at 1430 may be performed at random or in the order of the flow region number (i.e., R). Once all pixels of all flow areas are individually identified and recorded, energy functions may be calculated and aliasing corrections may be applied to the flow areas as previously discussed.

Figure 3:
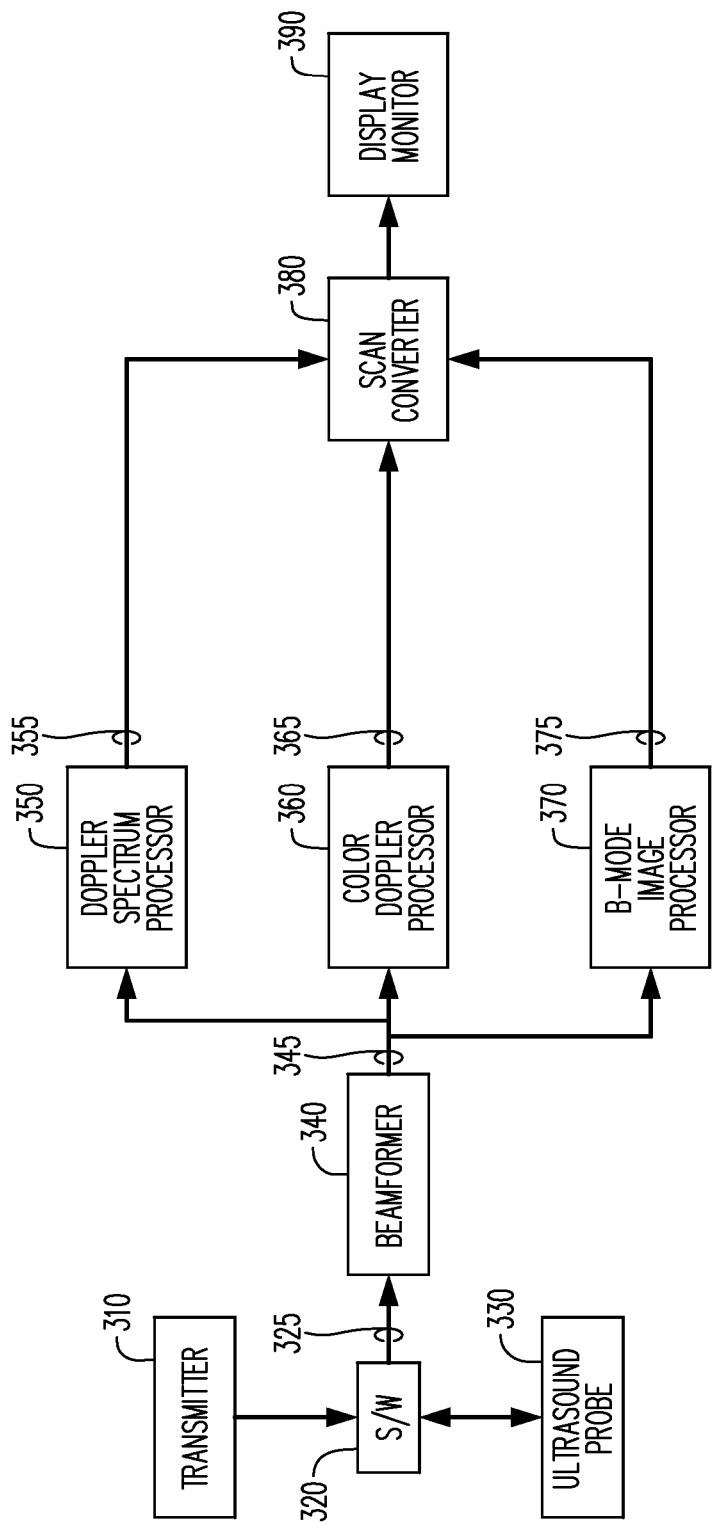
FIG. 3: A diagram of an ultrasound diagnostic imaging system (prior art).

FIG. 3 shows a diagram of a conventional ultrasound diagnostic imaging system with B-mode imaging, Doppler spectrum and color Doppler imaging (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768, 515, U.S. Pat. No. 4,771,789, U.S. Pat. No. 4,780,837, U.S.

Pat. No. 4,799,490, and U.S. Pat. No. 4,961,427). The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter 310 through a transmit/receive switch 320. The probe 320 may consist of an array of transducer elements which are separately driven by the transmitter with different time-delays so that a transmit ultrasound beam is focused and steered. A beamformer 340 receives the received ultrasound signal(s) from the probe 330 through the switch 320 and processes the signal(s) 325. The beamformer applies delays and/or phases to the signals and the resultant signals are summed for focusing and steering a receive ultrasound beam. The beamformer may also apply apodization, amplification and filtering.

The processed signal 345 is coupled to a Doppler spectrum processor 350, a color flow processor 360, and a B-mode image processor 370. The Doppler spectrum processor 350 includes a Doppler signal processor and a spectrum analyzer, and processes Doppler flow velocity signals and calculates and outputs a Doppler spectrum 355. The color flow processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color flow processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

Figure 4:
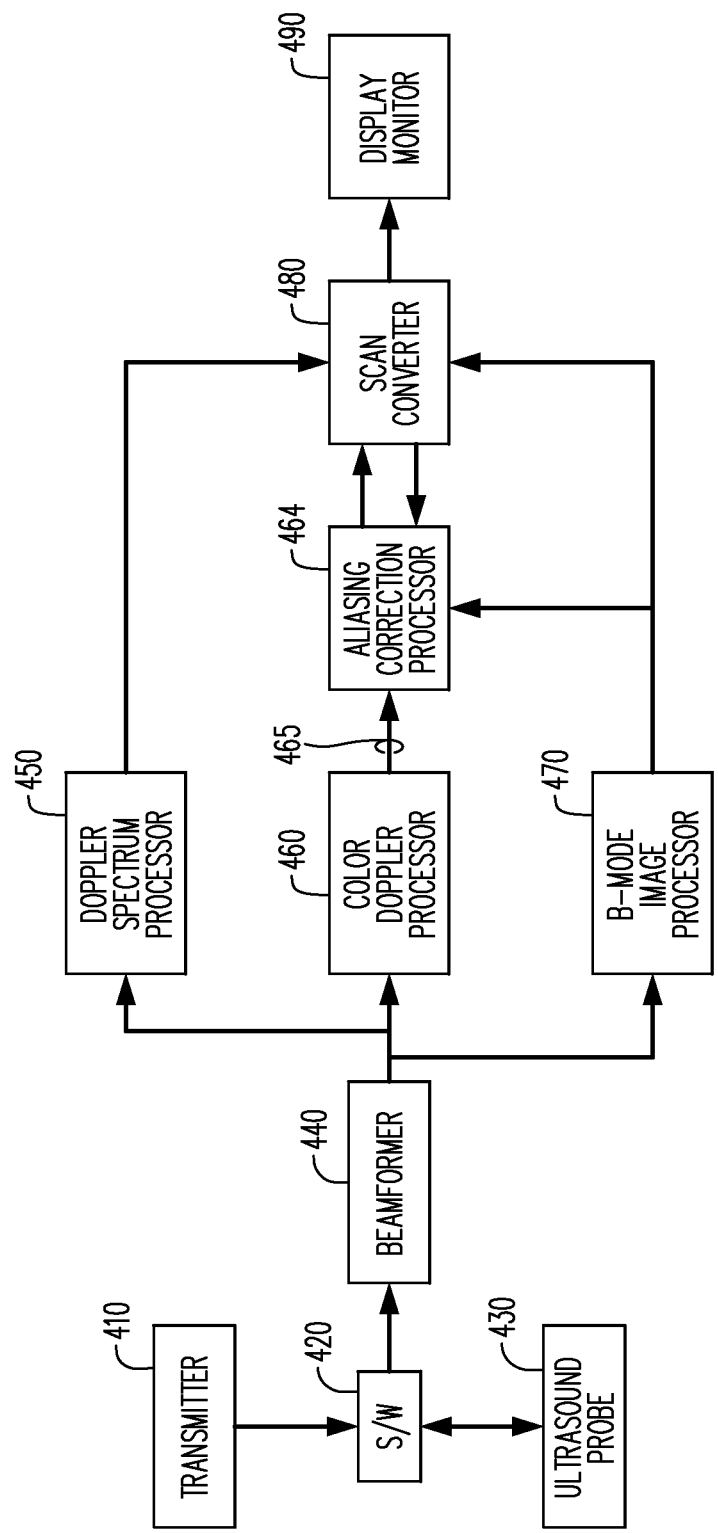
FIG. 4: A diagram of an ultrasound diagnostic imaging system according to some embodiments and using line data.
Figure 5:
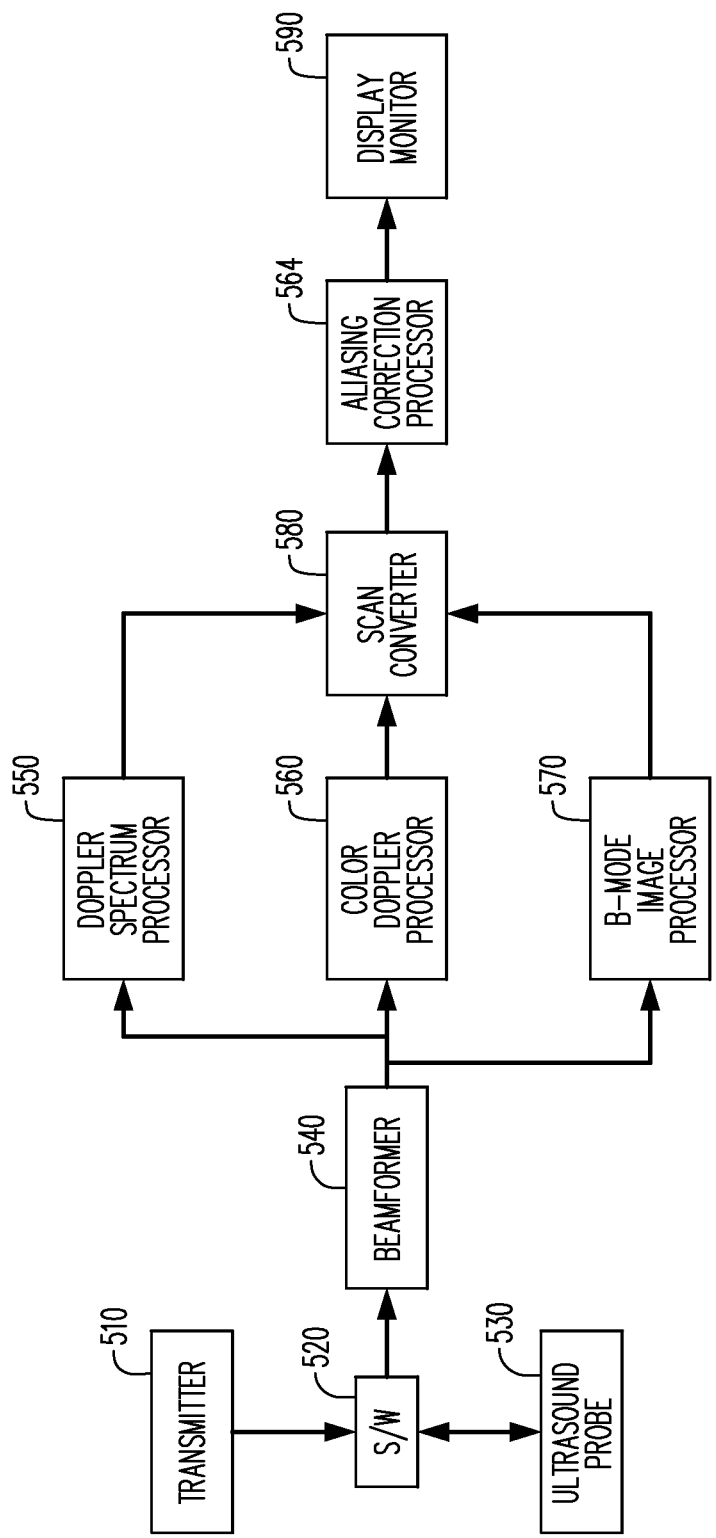
FIG. 5: A diagram of an ultrasound diagnostic imaging system according to some embodiments and using scan-converted images.

FIG. 4 shows a diagram of an ultrasound imaging system including a color Doppler aliasing correction processor 464 according to some embodiments. The aliasing correction processor 464 may perform the method described previously with respect to color flow line data as described above. The aliasing correction processor 464 receives output 465 from the color Doppler processor 460 as well as the scan-converted B-mode image from the scan converter 480. Output 465 comprises color flow line data rather than the scan-converted color Doppler image. FIG. 5 shows a diagram of embodiments in which the testing and correction of color Doppler aliasing is performed in the scan-converted image domain rather than the line data domain which was discussed previously. The B-mode image and color Doppler image are scan-converted before the aliasing correction processor 564 performs processing thereon.

One or more embodiments have been described. Nevertheless, various modifications will be apparent to those in the art.

The invention claimed is:

1. A method implemented by an imaging system, comprising:
   acquiring color Doppler data;
   detecting one or more border pixels of the color Doppler data;
   associating each of the one or more border pixels with a respective one of one or more borders;
   selecting a flow area bounded by a first one of the one or more borders;
   selecting a first one of the one or more border pixels associated with the first border;
   detecting a pixel adjacent to the first border pixel, determining whether the adjacent pixel is not one of the one or more border pixels, and, in response to determining that the adjacent pixel is not one of the one or more border pixels, associating the adjacent pixel with the selected flow area;
   detecting a second pixel adjacent to the adjacent pixel, determining whether the second pixel is not one of the one or more border pixels, and, in response to determining that the second pixel is not one of the one or more border pixels, associating the second pixels with the selected flow area; and
   detecting a third pixel adjacent to the second pixel, determining whether the third pixel is not one of the one or more border pixels, and, in response to determining that the third pixel is not one of the one or more border pixels, and associating the third pixel with the selected flow area.

2. A method according to claim 1, wherein associating the second pixels with the selected flow area comprises:
   logically associating adjacent ones of the second pixels with each other in memory.

3. A method according to claim 1, further comprising:
   selecting a third one of the one or more border pixels associated with the first border;
   detecting a fourth pixel adjacent to the second border pixel, determining whether the fourth adjacent pixel is not one of the one or more border pixels, and, in response to determining that the fourth adjacent pixel is not one of the one or more border pixels, associating the fourth adjacent pixel with the selected flow area; and
   detecting fifth pixels adjacent to the fourth adjacent pixel and associating the fifth pixels with the selected flow area until a fourth one of the one or more border pixels associated with the first border is detected.

4. A method according to claim 1, further comprising:
   selecting a second flow area bounded by a second one of the one or more borders;
   selecting a third one of the one or more border pixels associated with the second border;
   detecting a fourth pixel adjacent to the second border pixel, determining whether the fourth adjacent pixel is not one of the one or more border pixels, and, in response to determining that the fourth adjacent pixel is not one of the one or more border pixels, associating the fourth adjacent pixel with the selected second flow area; and
   detecting fifth pixels adjacent to the fourth adjacent pixel and associating the fifth pixels with the second selected flow area until a fourth one of the one or more border pixels associated with the second border is detected.

5. A method according to claim 1, wherein one or more of the border pixels are associated with one of the adjacent flow areas.

6. A method according to claim 1, wherein one or more of the border pixels of one flow area are associated with one or more of border pixels of adjacent flow areas.

7. A method according to claim 6, wherein a color Doppler velocity of one or more of the border pixels of one flow area is associated with a color Doppler velocity of one or more of border pixels of an adjacent flow area.

8. A method according to claim 1, further comprising:
   applying a first set of aliasing corrections to the color Doppler data to generate second color Doppler data;
   for each of the one or more borders, determining one or more pairs of color Doppler values in the second color Doppler data, wherein each color Doppler value of a pair of color Doppler values is located on opposite sides of a border;
   for each of the one or more borders, evaluating a first energy function based on the one or more pairs of color Doppler values in the second color Doppler data, wherein each color Doppler value of a pair of color Doppler values is located on opposite sides of a border;

evaluating a first total energy function associated with the first set of aliasing corrections based on the evaluated first energy functions;

applying a second set of aliasing corrections to the color Doppler data to generate third color Doppler data;

for each of the one or more borders, determining one or more pairs of color Doppler values in the third color Doppler data, wherein each color Doppler value of a pair of color Doppler values is located on opposite sides of a border;

for each of the one or more borders, evaluating a second energy function based on the one or more pairs of color Doppler values in the third color Doppler data, wherein each color Doppler value of a pair of color Doppler values is located on opposite sides of a border; and evaluating a second total energy function associated with the second set of aliasing corrections based on the evaluated second energy functions.

9. A method according to claim 8, wherein the acquired color Doppler data comprises color flow line data or scan-converted color flow image data.

10. A method according to claim 8, wherein the acquired color Doppler values comprise color flow velocities, Doppler shift frequencies or color Doppler phases.

11. A method according to claim 8, wherein evaluation of the first energy function for a border comprises:
calculation of the sum of the absolute differences between each of the one or more pairs of color Doppler values which are located on opposite sides of the border.

12. A method according to claim 8, wherein evaluation of the first energy function for a border comprises:
calculation of the sum of the p-th power of the absolute differences between each of the one or more pairs of color Doppler values which are located on opposite sides of the border.

13. A method according to claim 8, wherein evaluation of the first total energy function comprises:
multiplying each of the first energy functions by a respective weight to obtain a respective product; and
adding the respective products.

14. A method according to claim 8, wherein the first set of aliasing corrections may comprise one or more of 0, $f_{PRF}$, $-f_{PRF}$, $2f_{PRF}$, $-2f_{PRF}$, $3f_{PRF}$, $-3f_{PRF}$, $4f_{PRF}$, $-4f_{PRF}$, $5f_{PRF}$ and $-5f_{PRF}$ of the Doppler shift frequency or one or more of 0, $V_{PRF}$, $-V_{PRF}$, $2V_{PRF}$, $-2V_{PRF}$, $3V_{PRF}$, $-3V_{PRF}$, $4V_{PRF}$, $-4V_{PRF}$, $5V_{PRF}$ and $-5V_{PRF}$ of color Doppler velocity or one or more of 0, $2\pi$, $-2\pi$, $4\pi$, $-4\pi$, $6\pi$, $-6\pi$, $8\pi$, $-8\pi$, $10\pi$ and $-10\pi$ of the color Doppler phase.

15. A method according to claim 8, further comprising:
identifying the first set of aliasing corrections as a correct set of aliasing corrections if the first total energy function is less than the second total energy function, and identifying the second set of aliasing corrections as the correct set of aliasing corrections if the second total energy function is less than the first total energy function.

16. A method according to claim 8, wherein the first total energy function associated with the first set of aliasing corrections is determined by summing the evaluated first energy functions.

17. A method according to claim 8, wherein the second total energy function associated with the second set of aliasing corrections is determined by summing the evaluated second energy functions.

18. A system comprising;
an aliasing correction processor to:
acquire color Doppler data;
detect one or more border pixels of the color Doppler data;
associate each of the one or more border pixels with a respective one of one or more borders;
select a flow area bounded by a first one of the one or more borders;
select a first one of the one or more border pixels associated with the first border;
detect a pixel adjacent to the first border pixel, determine whether the adjacent pixel is not one of the one or more border pixels, and, in response to the determination that the adjacent pixel is not one of the one or more border pixels, associate the adjacent pixel with the selected flow area;
detect a second pixel adjacent to the adjacent pixel, determine whether the second pixel is not one of the one or more border pixels, and, in response to determining that the second pixel is not one of the one or more border pixels, associate the second pixels with the selected flow area; and
detecting a third pixel adjacent to the second pixel, determining whether the third pixel is not one of the one or more border pixels, and, in response to determining that the third pixel is not one of the one or more border pixels, and associating the third pixel with the selected flow area.

19. A system according to claim 18, wherein associating the second pixels with the selected flow area comprises:
logically associating adjacent ones of the second pixels with each other in memory.

20. A system according to claim 18, the aliasing correction processor further to:
select a third one of the one or more border pixels associated with the first border;
detect a fourth pixel adjacent to the second border pixel, determine whether the fourth adjacent pixel is not one of the one or more border pixels, and, in response to the determination that the fourth adjacent pixel is not one of the one or more border pixels, associate the fourth adjacent pixel with the selected flow area; and
detect fifth pixels adjacent to the fourth adjacent pixel and associate the fifth pixels with the selected flow area until a fourth one of the one or more border pixels associated with the first border is detected.

21. A system according to claim 18, the aliasing correction processor further to:
select a second flow area bounded by a second one of the one or more borders;
select a third one of the one or more border pixels associated with the second border;
detect a fourth pixel adjacent to the second border pixel, determine whether the fourth adjacent pixel is not one of the one or more border pixels, and, in response to the determination that the fourth adjacent pixel is not one of the one or more border pixels, associate the fourth adjacent pixel with the selected second flow area; and
detect fifth pixels adjacent to the fourth adjacent pixel and associate the fifth pixels with the second selected flow area until a fourth one of the one or more border pixels associated with the second border is detected.

22. A system according to claim 18, wherein one or more of the border pixels are associated with one of the adjacent flow areas.

23. A system according to claim 18, wherein one or more of the border pixels of one flow area are associated with one or more of border pixels of adjacent flow areas.

24. A system according to claim 23, wherein a color Doppler velocity of one or more of the border pixels of one flow area is associated with a color Doppler velocity of one or more of border pixels of an adjacent flow area.

25. A system according to claim 18, the aliasing correction processor further to:
apply a first set of aliasing corrections to the color Doppler data to generate second color Doppler data;
for each of the one or more borders, determine one or more pairs of color Doppler values in the second color Doppler data which are located on opposite sides of the border;
for each of the one or more borders, evaluate a first energy function based on the one or more pairs of color Doppler values in the second color Doppler data which are located on opposite sides of the border;
evaluate a first total energy function associated with the first set of aliasing corrections based on the evaluated first energy functions;
apply a second set of aliasing corrections to the color Doppler data to generate third color Doppler data;
for each of the one or more borders, determine one or more pairs of color Doppler values in the third color Doppler data which are located on opposite sides of the border;
for each of the one or more borders, evaluate a second energy function based on the one or more pairs of color Doppler values in the third color Doppler data which are located on opposite sides of the border; and
evaluate a second total energy function associated with the second set of aliasing corrections based on the evaluated second energy functions.

26. A system according to claim 25, wherein the acquired color Doppler data comprises color flow line data or scan-converted color flow image data.

27. A system according to claim 25, wherein the acquired color Doppler values may comprise color flow velocities, Doppler shift frequencies or color Doppler phases.

28. A system according to claim 25, wherein evaluation of the first energy function for a border comprises:
calculation of the sum of the absolute differences between each of the one or more pairs of color Doppler values which are located on opposite sides of the border.

29. A system according to claim 25, wherein evaluation of the first energy function for a border comprises:
calculation of the sum of the p-th power of the absolute differences between each of the one or more pairs of color Doppler values which are located on opposite sides of the border.

30. A system according to claim 25, wherein evaluation of the first total energy function comprises:
multiplying each of the first energy functions by a respective weight to obtain a respective product; and
adding the respective products.

31. A system according to claim 25, wherein the first set of aliasing corrections may comprise one or more of 0, $f_{PRF}$, $-f_{PRF}$, $2f_{PRF}$, $-2f_{PRF}$, $3f_{PRF}$, $-3f_{PRF}$, $4f_{PRF}$, $-4f_{PRF}$, $5f_{PRF}$ and $-5f_{PRF}$ of the Doppler shift frequency or
one or more of 0, $V_{PRF}$, $-V_{PRF}$, $2V_{PRF}$, $-2V_{PRF}$, $3V_{PRF}$, $-3V_{PRF}$, $4V_{PRF}$, $-4V_{PRF}$, $5V_{PRF}$ and $-5V_{PRF}$ of color Doppler velocity or
one or more of 0, $2\pi$, $-2\pi$, $4\pi$, $-4\pi$, $6\pi$, $-6\pi$, $8\pi$, $-8\pi$, $10\pi$ and $-10\pi$ of the color Doppler phase.

32. A system according to claim 25, the aliasing correction processor further to:
identifying the first set of aliasing corrections as a correct set of aliasing corrections if the first total energy function is less than the second total energy function, and identifying the second set of aliasing corrections as the correct set of aliasing corrections if the second total energy function is less than the first total energy function.

33. A system according to claim 25, wherein the first total energy function associated with the first set of aliasing corrections is determined by summing the evaluated first energy functions.

34. A system according to claim 25, wherein the second total energy function associated with the second set of aliasing corrections is determined by summing the evaluated second energy functions.

* * * * *